(12) United States Patent
Wager et al.

(10) Patent No.: US 8,178,574 B2
(45) Date of Patent: May 15, 2012

(54) TOSYLATE SALT OF TRANS-N-ISOBUTYL-3-FLUORO-3-[3-FLUORO-4-(PYRROLIDIN-1-YL-METHYL)-PHENYL] CYCLOBUTANECARBOXAMIDE

(75) Inventors: Travis T. Wager, New London, CT (US); Todd W. Butler, Salem, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 12/745,982

(22) PCT Filed: Dec. 4, 2008

(86) PCT No.: PCT/IB2008/003392
§ 371 (c)(1),
(2), (4) Date: Jun. 3, 2010

(87) PCT Pub. No.: WO2009/071988
PCT Pub. Date: Jun. 11, 2009

(65) Prior Publication Data
US 2010/0256213 A1    Oct. 7, 2010

Related U.S. Application Data (60) Provisional application No. 61/005,696, filed on Dec. 7, 2007.

(51) Int. Cl.
A61K 31/40 (2006.01)
C07D 207/08 (2006.01)
A61P 25/00 (2006.01)
A61P 11/00 (2006.01)
A61P 37/08 (2006.01)
A61P 9/00 (2006.01)
A61P 1/04 (2006.01)

(52) U.S. Cl. ........................ 514/408; 548/578
(58) Field of Classification Search .................. None
See application file for complete search history.

(56) References Cited

U.S. PATENT DOCUMENTS
2008/0096955 A1 * 4/2008 Wager et al. .................. 514/422

FOREIGN PATENT DOCUMENTS
WO   WO 2007049123   5/2007
WO   WO 2008090429   7/2008

OTHER PUBLICATIONS
Chawla et al., CRIPS vol. 5, No. 1, Jan.-Mar. 2004, p. 9-12.*
Newman et al., DDT vol. 8, Oct. 2003, p. 898-905.*

* cited by examiner

Primary Examiner — Sun Jae Loewe
(74) Attorney, Agent, or Firm — Gregg C. Benson; John A. Wichtowski (57) ABSTRACT

The present invention is directed to the tosylate salt of trans-N-isobutyl-3-fluoro-3-[3-fluoro-4-(pyrrolidin-1-ylmethyl)-phenyl]-cyclobutanecarboxamide Formula (I):

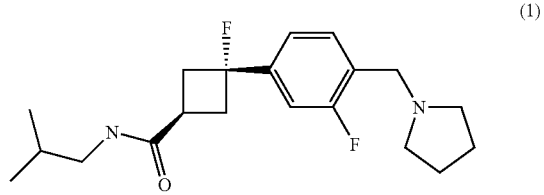

to solvates (e.g., hydrates) thereof, to polymorphs thereof, to pharmaceutical compositions thereof and to a method of treating depression, mood disorders, schizophrenia, anxiety disorders, cognitive disorders, Alzheimer's disease, attention-deficit disorder (ADD), attention-deficit hyperactivity disorder (ADHD), psychotic disorders, sleep disorders, obesity, dizziness, epilepsy, motion sickness, respiratory diseases, allergy, allergy-induced airway responses, allergic rhinitis, nasal congestion, allergic congestion, congestion, hypotension, cardiovascular disease, diseases of the GI tract, hyper- and hypo-motility and acidic secretion of the gastrointestinal tract comprising administering a therapeutically effective amount thereof.

2 Claims, 6 Drawing Sheets

FIG. 1

| Caption | Legend | Angle | d value | Intensity | Intensity % |
|---|---|---|---|---|---|
| | | 2-Theta ° | Angstrom | Count | % |
| d=14.04179 | | 6.289 | 14.04179 | 158 | 2.9 |
| d=10.58016 | | 8.35 | 10.58016 | 5533 | 100 |
| d=9.49601 | | 9.305 | 9.49601 | 584 | 10.6 |
| d=9.29045 | | 9.512 | 9.29045 | 396 | 7.2 |
| d=7.94430 | | 11.128 | 7.9443 | 508 | 9.2 |
| d=7.73290 | | 11.434 | 7.7329 | 241 | 4.4 |
| d=7.30641 | | 12.103 | 7.30641 | 507 | 9.2 |
| d=7.06253 | | 12.523 | 7.06253 | 108 | 2 |
| d=6.81235 | | 12.985 | 6.81235 | 166 | 3 |
| d=6.60181 | | 13.401 | 6.60181 | 977 | 17.7 |
| d=6.20605 | | 14.26 | 6.20605 | 104 | 1.9 |
| d=5.94020 | | 14.901 | 5.9402 | 266 | 4.8 |
| d=5.75800 | | 15.376 | 5.758 | 379 | 6.8 |
| d=5.66127 | | 15.64 | 5.66127 | 267 | 4.8 |
| d=5.55295 | | 15.947 | 5.55295 | 230 | 4.2 |
| d=5.31030 | | 16.681 | 5.3103 | 3188 | 57.6 |
| d=4.89868 | | 18.094 | 4.89868 | 616 | 11.1 |
| d=4.78866 | | 18.513 | 4.78866 | 630 | 11.4 |
| d=4.64380 | | 19.096 | 4.6438 | 2038 | 36.8 |
| d=4.52966 | | 19.582 | 4.52966 | 711 | 12.9 |
| d=4.31232 | | 20.579 | 4.31232 | 1045 | 18.9 |
| d=4.12213 | | 21.54 | 4.12213 | 1823 | 32.9 |
| d=3.99927 | | 22.21 | 3.99927 | 2169 | 39.2 |
| d=3.89440 | | 22.816 | 3.8944 | 320 | 5.8 |
| d=3.79457 | | 23.424 | 3.79457 | 279 | 5 |
| d=3.74079 | | 23.766 | 3.74079 | 719 | 13 |
| d=3.67975 | | 24.166 | 3.67975 | 287 | 5.2 |
| d=3.57685 | | 24.872 | 3.57685 | 767 | 13.9 |
| d=3.49127 | | 25.492 | 3.49127 | 423 | 7.6 |
| d=3.42060 | | 26.028 | 3.4206 | 723 | 13.1 |
| d=3.28099 | | 27.156 | 3.28099 | 432 | 7.8 |
| d=3.17747 | | 28.059 | 3.17747 | 245 | 4.4 |
| d=3.10497 | | 28.728 | 3.10497 | 279 | 5 |
| d=3.04108 | | 29.345 | 3.04108 | 251 | 4.5 |
| d=2.93897 | | 30.388 | 2.93897 | 275 | 5 |
| d=2.91555 | | 30.639 | 2.91555 | 240 | 4.3 |
| d=2.88300 | | 30.993 | 2.883 | 170 | 3.1 |
| d=2.82775 | | 31.614 | 2.82775 | 153 | 2.8 |
| d=2.77843 | | 32.191 | 2.77843 | 128 | 2.3 |
| d=2.73208 | | 32.752 | 2.73208 | 260 | 4.7 |
| d=2.65861 | | 33.684 | 2.65861 | 167 | 3 |
| d=2.60906 | | 34.343 | 2.60906 | 170 | 3.1 |
| d=2.54088 | | 35.294 | 2.54088 | 205 | 3.7 |
| d=2.48301 | | 36.145 | 2.48301 | 173 | 3.1 |
| d=2.41051 | | 37.271 | 2.41051 | 126 | 2.3 |
| d=2.38225 | | 37.73 | 2.38225 | 110 | 2 |
| d=2.33660 | | 38.496 | 2.3366 | 105 | 1.9 |
| d=2.27937 | | 39.502 | 2.27937 | 82 | 1.5 |

VTI Moisture Sorption Data

| | |
|---|---|
| File Name | 03282006.Vlsh |
| Experiment | Step Isotherm |
| Operator | ac |
| Experiment ID | 03282006 |
| Adsorbate | Water |
| Sample Lot # | 00110012-57-3 |
| Notes | |
| Drying Temp | 25 °C |
| Heating Rate | 1 °C/min |
| Max Drying Time | 120 min |
| Equil Crit | 0.0010 wt % in      5.00 min |
| Expt Temp | 25 °C |
| Max Equil Time | 120 min |
| EquilCrit | 0.0010 wt % in      5.00 min |
| RH Steps | 5, 10, 15, 20, 25, 30, 35, 40, 45, 50, 55, 50, 65, 70, 75, 80, 85, 90, 80, 70, 50, 50,40,30,20, 10 |
| Data Logging Interval | 1.00 min or      0.0100 wt % |
| Expt Slarted | 03/28/2006 |
| Run Started | 13:23:56 |

FIG. 5

| Elap Time min | Weight mg | Weight % chg | Press Torr | Temp deg C | RH |
|---|---|---|---|---|---|
| 197.9 | 17.1719 | 0.000 | 0.03 | 25.38 | 0.14 |
| 238.4 | 17.1750 | 0.018 | 4.14 | 25.14 | 17.29 |
| 300.8 | 17.1691 | -0.016 | 2.45 | 25.14 | 10.21 |
| 330.6 | 17.1710 | -0.005 | 3.58 | 25.22 | 14.87 |
| 350.4 | 17.1724 | 0.003 | 4.77 | 25.19 | 19.85 |
| 472.0 | 17.1801 | 0.048 | 6.05 | 25.16 | 25.22 |
| 493.0 | 17.1816 | 0.057 | 7.20 | 25.20 | 29.94 |
| 614.5 | 17.1892 | 0.101 | 8.41 | 25.11 | 35.14 |
| 736.0 | 17.1965 | 0.143 | 9.52 | 25.11 | 39.78 |
| 785.3 | 17.1973 | 0.148 | 10.75 | 25.13 | 44.87 |
| 816.6 | 17.1975 | 0.149 | 11.98 | 25.18 | 49.84 |
| 845.6 | 17.1977 | 0.150 | 13.12 | 25.12 | 54.78 |
| 885.8 | 17.1981 | 0.153 | 14.32 | 25.11 | 59.84 |
| 954.2 | 17.2008 | 0.168 | 15.57 | 25.18 | 64.79 |
| 1076.3 | 17.2092 | 0.217 | 16.73 | 25.13 | 69.83 |
| 1198.4 | 17.2193 | 0.276 | 17.99 | 25.14 | 75.04 |
| 1320.6 | 17.2316 | 0.348 | 19.17 | 25.15 | 79.90 |
| 1442.8 | 17.2443 | 0.422 | 20.55 | 25.23 | 85.26 |
| 1565.4 | 17.2573 | 0.497 | 21.57 | 25.16 | 89.83 |
| 1687.5 | 17.2572 | 0.497 | 19.14 | 25.15 | 79.80 |
| 1737.6 | 17.2570 | 0.495 | 16.79 | 25.17 | 69.88 |
| 1799.7 | 17.2567 | 0.494 | 14.41 | 25.14 | 60.13 |
| 1917.9 | 17.2555 | 0.487 | 12.05 | 25.20 | 50.09 |
| 2042.5 | 17.2523 | 0.468 | 9.63 | 25.12 | 40.22 |
| 2169.6 | 17.2424 | 0.411 | 7.23 | 25.12 | 30.18 |
| 2303.2 | 17.2248 | 0.308 | 4.85 | 25.12 | 20.24 |
| 2433.0 | 17.2015 | 0.173 | 2.44 | 25.11 | 10.19 |

TOSYLATE SALT OF TRANS-N-ISOBUTYL-3-FLUORO-3-[3-FLUORO-4-(PYRROLIDIN-1-YL-METHYL)-PHENYL] CYCLOBUTANECARBOXAMIDE

This application is a national stage filing of PCT/IB2008/003392 filed Dec. 4, 2008, which claims the benefit of Provisional Patent Application No. 61/005,696 filed Dec. 7, 2007.

The present invention is directed to the tosylate salt of the compound of formula 1 as described herein, to a pharmaceutical composition comprising this preferred salt, and to methods of treatment of disorders or conditions that may be treated by antagonizing histamine-3 ($H_3$) receptors using such preferred pharmaceutical compositions.

Histamine is a well-known mediator in hypersensitive reactions (e.g. allergies, hay fever, and asthma) that are commonly treated with antagonists of histamine or "antihistamines." It has also been established that histamine receptors exist in at least two distinct types, referred to as $H_1$ and $H_2$ receptors.

A third histamine receptor ($H_3$ receptor) is believed to play a role in neurotransmission in the central nervous system, where the $H_3$ receptor is thought to be disposed presynaptically on histaminergic nerve endings (*Nature,* 302, S32-S37 (1983)). The existence of the $H_3$ receptor has been confirmed by the development of selective $H_3$ receptor agonists and antagonists (*Nature,* 327, 117-123 (1987)) and has subsequently been shown to regulate the release of the neurotransmitters in both the central nervous system and peripheral organs, particularly the lungs, cardiovascular system and gastrointestinal tract.

A number of diseases or conditions may be treated with histamine-3 receptor ligands wherein the $H_3$ ligand may be an antagonist, agonist or partial agonist, see: (Imamura et al., *Circ. Res.,* (1996) 78, 475-481); (Imamura et. al., *Circ. Res.,* (1996) 78, 863-869); (Lin et al., *Brain Res.* (1990) 523, 325-330); (Monti et al., *Neuropsychopharmacology* (1996) 15, 31 35); (Sakai, et al., *Life Sci.* (1991) 48, 2397-2404); (Mazurkiewicz-Kwilecki and Nsonwah, *Can. J. Physiol. Pharmacol.* (1989) 67, 75-78); (Panula, P. et al., *Neuroscience* (1998) 44, 465-481); (Wads et al., *Trends in Neuroscience* (1991) 14, 415); (Monti et al., *Eur. J. Pharmacol.* (1991) 205, 283); (Haas et al., *Behav. Brain Res.* (1995) 66, 41-44); (De Almeida and Izquierdo, *Arch. Int. Pharmacodyn.* (1986) 283, 193-198); (Kamei et al., *Psychopharmacology* (1990) 102, 312-318); (Kamei and Sakata, Japan. *J. Pharmacol.* (1991) 57, 437-482); (Schwartz et al., *Psychopharmacology; The Fourth Generation of Progress,* Bloom and Kupfer (eds.), Raven Press, New York, (1995) 397); (Shaywitz et al., *Psychopharmacology* (1984) 82, 73-77); (Dumery and Blozovski, *Exp. Brain Res.* (1987) 67, 61-69); (Tedford et al, *J. Pharmacol. Exp. Ther.* (1995) 275, 598-604); (Tedford et al., *Soc. Neurosci. Abstr.* (1996) 22, 22); (Yokoyama et al., *Eur. J. Pharmacol.* (1993) 234, 129); (Yokoyama and Iinuma, *CNS Drugs* (1996) 5, 321); (Onodera et al., *Prog. Neurobiol.* (1994) 42, 685); (Leurs and Timmerman, *Prog. Drug Res.* (1992) 39, 127); (*The Histamine H*3 *Receptor,* Leurs and Timmerman (ed.), Elsevier Science, Amsterdam (1998); (Leurs et al., *Trends in Pharm. Sci.* (1998) 19, 177-183); (Phillips at al., *Annual Reports in Medicinal Chemistry* (1998) 33, 31-40); (Matsubara et al., *Eur. J. Pharmacol.* (1992) 224, 145); (Rouleau et al., *J. Pharmacol. Exp. Ther.* (1997) 281, 1085); (A. Szelag, "Role of histamine H3-receptors in the proliferation of neoplastic cells in vitro", *Med. Sci. Monit.,* 4(5):747-755, (1998)); (C. Fitzsimons, H. Duran, F. Labombarda, B. Molinari and E. Rivera, "Histamine receptors signalling in epidermal tumor cell lines with H-ras gene alterations", *Inflammation Res.,* 47 (Suppl. 1): S50-S51, (1998)); (R. Leurs, R. C. Vollinga and H. Timmerman, "The medicinal chemistry and therapeutic potentials of ligand of the histamine H3 receptor", *Progress in Drug Research* 45: 170, (1995)); (R. Levi and N. C. E. Smith, "Histamine H3-receptors: A new frontier in myocardial ischemia", *J. Pharm. Exp. Ther.,* 292: 825-830, (2000)); (Hatta, E., K. Yasuda and R. Levi, "Activation of histamine H3 receptors inhibits carrier-mediated norepinephrine release in a human model of protracted myocardial ischemia", *J. Pharm. Exp. Ther.,* 283: 494-500, (1997); (H. Yokoyama and K. Iinuma, "Histamine and Seizures: Implications for the treatment of epilepsy", *CNS Drugs,* 5(5); 321-330, (1995)); (K. Hurukami, H. Yokoyama, K. Onodera, K. Iinuma and T. Watanabe, AQ-0 145, "A newly developed histamine H3 antagonist, decreased seizure susceptibility of electrically induced convulsions in mice", *Meth. Find. Exp. Clin. Pharmacol.,* 17(C): 70-73, (1995); (Delaunois A., Gustin P., Garbarg M., and Ansay M., "Modulation of acetylcholine, capsaicin and substance P effects by histamine H3 receptors in isolated perfused rabbit lungs", *European Journal of Pharmacology* 277(2-3):243-50, (1995)); and (Dimitriadou, et al., "Functional relationship between mast cells and C-sensitive nerve fibres evidenced by histamine H3-receptor modulation in rat lung and spleen", *Clinical Science* 87(2):151-63, (1994). Such diseases or conditions include cardiovascular disorders such as acute myocardial infarction; memory processes, dementia and cognitive disorders such as Alzheimer's disease and attention-deficit hyperactivity disorder; neurological disorders such as Parkinson's disease, schizophrenia, depression, epilepsy, and seizures or convulsions; cancer such as cutaneous carcinoma, medullary thyroid carcinoma and melanoma; respiratory disorders such as asthma; sleep disorders such as narcolepsy; vestibular dysfunction such as Meniere's disease; gastrointestinal disorders, inflammation, migraine, motion sickness, obesity, pain, and septic shock.

H3 receptor antagonists have also been previously described in, for example, WO 03/050099, WO 02/0769252, WO 02/12224, and U.S. Patent Publication No. 2005/0171181 A1. The histamine $H_3$ receptor (H3R) regulates the release of histamine and other neurotransmitters, including serotonin and acetylcholine. H3R is relatively neuron specific and inhibits the release of certain monoamines such, as histamine. Selective antagonism of H3R receptors raises brain histamine levels and inhibits such activities as food consumption while minimizing non-specific peripheral consequences. Antagonists of the receptor increase synthesis and release of cerebral histamine and other monoamines. By this mechanism, they induce a prolonged wakefulness, improved cognitive function, reduction in food intake and normalization of vestibular reflexes. Accordingly (although the uses described herein are by no means limited by these stated mechanisms), the receptor is an important target for new therapeutics in Alzheimer disease, mood and attention adjustments, including attention deficit hyperactive disorder (ADHD), cognitive deficiencies, obesity, dizziness, schizophrenia, epilepsy, sleeping disorders, narcolepsy and motion sickness, and various forms of anxiety.

The majority of histamine $H_3$ receptor antagonists to date resemble histamine in possessing an imidazole ring that may be substituted, as described, for example, in WO 96/38142. Non-imidazole neuroactive compounds such as beta histamines (Arrang, Eur. J. Pharm. 1985, 111:72-84) demonstrated some histamine $H_3$ receptor activity but with poor potency. EP 978512 and EP 0982300A2 disclose non-imidazole alkyamines as histamine H3 receptor antagonists. WO 02/12224 (Ortho McNeil Pharmaceuticals) describes non-imidazole bicyclic derivatives as histamine H₃ receptor ligands. Other receptor antagonists have been described in WO 02/32893 and WO 02/06233.

Compounds that are antagonists of the histamine-3 receptor, including trans-N-isobutyl-3-fluoro-3-[3-fluoro-4-(pyrrolidin-1-ylmethyl)phenyl]cyclobutanecarboxamide, and its hydro-chloride salt, and other related active compounds, are referred to in U.S. Ser. No. 11/549,175, filed Oct. 13, 2006. The foregoing application, owned in common with the present application and incorporated herein by reference in its entirety, generically recites pharmaceutically acceptable acid addition salts for the compounds referred to therein.

SUMMARY OF THE INVENTION

The present invention is directed to the tosylate salt of the compound of formula 1:

(1)

to solvates (e.g., hydrates) thereof, to polymorphs thereof, and to pharmaceutical compositions thereof. The compound of formula 1 may be referred to herein as trans-N-isobutyl-3-fluoro-3-[3-fluoro-4-(pyrrolidin-1-ylmethyl)phenyl]cyclobutanecarboxamide, which may also be referred to as (trans) 3-fluoro-3-[3-fluoro-4-(pyrrolidin-1-ylmethyl) phenyl]cyclobutanecarboxylic acid isobutyl amide.

The compound of formula 1 is an antagonist of the histamine-3 (H₃) receptor and is useful in the treatment of a number of disorders, diseases and conditions of the central nervous system. This compound is particularly useful in the treatment of a disorder or condition selected from the group consisting of depression, mood disorders, schizophrenia, anxiety disorders, cognitive disorders, Alzheimer's disease, attention-deficit disorder (ADD), attention-deficit hyperactivity disorder (ADHD), psychotic disorders, sleep disorders, obesity, dizziness, epilepsy, motion sickness, respiratory diseases, allergy, allergy-induced airway responses, allergic rhinitis, nasal congestion, allergic congestion, congestion, hypotension, cardiovascular disease, diseases of the GI tract, hyper- and hypo-motility and acidic secretion of the gastrointestinal tract.

In one embodiment, the tosylate salt of the invention is an anhydrous or nearly anhydrous polymorph.

The tosylate salt of the present invention exhibits properties, including those of solid-state stability and compatibility with certain drug product formulation excipients, that render it superior to previously known salts of trans-N-isobutyl-3-fluoro-3-[3-fluoro-4-(pyrrolidin-1-ylmethyl)phenyl]-cyclobutanecarboxamide.

The compound of formula 1 (trans-N-isobutyl-3-fluoro-3-[3-fluoro-4-(pyrrolidin-1-ylmethyl)phenyl]cyclobutanecarboxamide) may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compound of formula 1 may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together—see Chem. Commun., 17, 1889-1896, by O. Almarsson and M. J. Zaworotko (2004). For a general review of multi-component complexes, see J. Pharm. Sci., 64 (8), 1269-1288, by Haleblian (August 1975).

The compound of formula 1 may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO⁻Na⁺, —COO⁻K⁺, or —SO₃⁻Na⁺) or non-ionic (such as —N⁻N⁺(CH₃)₃) polar head group. For more information, see Crystals and the Polarizing Microscope by N. H. Hartshorne and A. Stuart, 4th Edition (Edward Arnold, 1970).

Figure 2A:
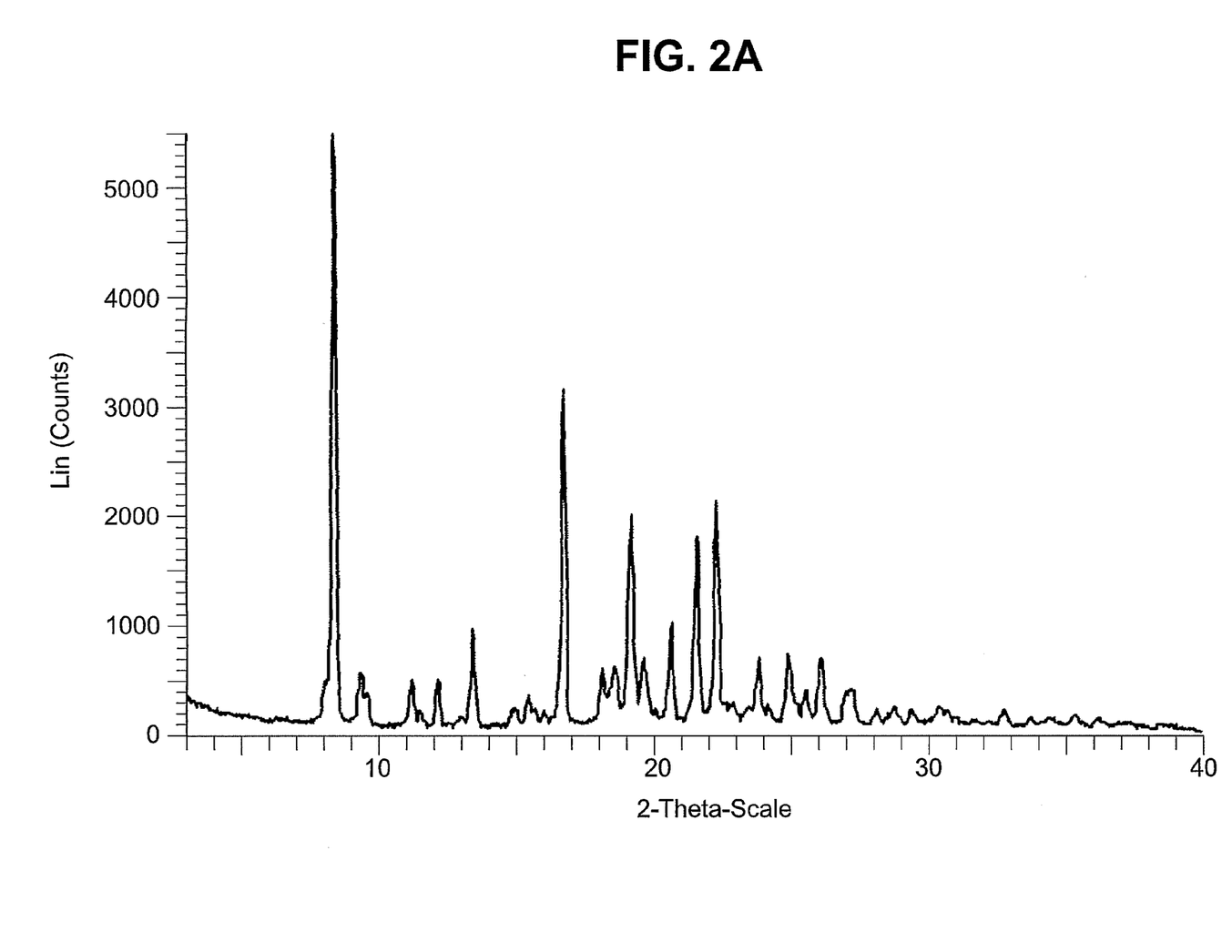
FIG. 2A is the observed X-ray powder diffraction pattern (y-axis is linear counts per second; X in degrees 2-theta) of the tosylate salt of trans-N-isobutyl-3-fluoro-3-[3-fluoro-4-(pyrrolidin-1-ylmethyl)phenyl]cyclobutanecarboxamide, with run conditions 2Th/Th locked, start 3.000 degrees, end 40.000 degrees, with steps of 0.040 degrees. Step time 1.s—at room temp (25° C.).
Figure 2B:
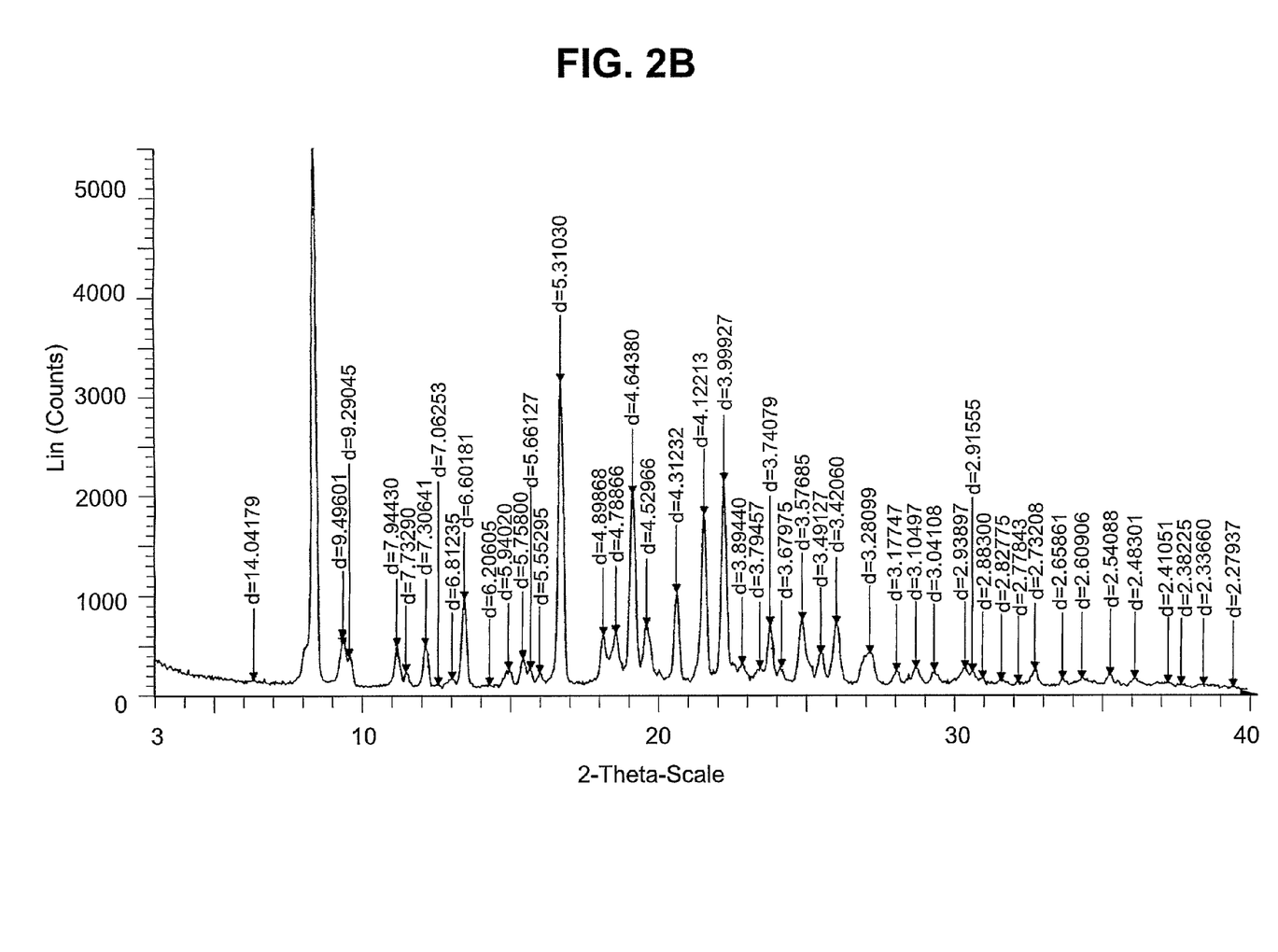
FIG. 2B identifies all the measured peaks (e.g. d=14.04179, d=10.58016) reported in FIG. 1, again with run conditions 2Th/Th locked, start 3.000 degrees, end 40.000 degrees, with steps of 0.040 degrees. Step time 1.s—at room temp (25° C.).

The tosylate salt of the invention is further characterized by the principal X-ray diffraction pattern peaks expressed in terms of 2θ as measured with copper radiation (within the margins of error indicated), as presented in Table I and FIGS. 1 and 2A/2B, and as discussed herein.

Hygroscopicity was assessed using a dynamic vapor sorption technique in which an accurately weighed sample is subjected to progressively changing water vapor pressure while simultaneously recording the weight change. The experiment is conducted isothermally at 25° C.

Another embodiment of the invention relates to a pharmaceutical composition comprising the tosylate salt of the compound of formula 1, and a pharmaceutically acceptable carrier or excipient, particularly one for the use in the treatment of depression, mood disorders, schizophrenia, anxiety disorders, cognitive disorders, Alzheimer's disease, attention-deficit disorder (ADD), attention-deficit hyperactivity disorder (ADHD), psychotic disorders, sleep disorders, obesity, dizziness, epilepsy, motion sickness, respiratory diseases, allergy, allergy-induced airway responses, allergic rhinitis, nasal congestion, allergic congestion, congestion, hypotension, cardiovascular disease, diseases of the GI tract, hyper- and hypo-motility and acidic secretion of the gastrointestinal tract.

The present invention further relates to a method of treating depression, mood disorders, schizophrenia, anxiety disorders, cognitive disorders, Alzheimer's disease, attention-deficit disorder (ADD), attention-deficit hyperactivity disorder (ADHD), psychotic disorders, sleep disorders, obesity, dizziness, epilepsy, motion sickness, respiratory diseases, allergy, allergy-induced airway responses, allergic rhinitis, nasal congestion, allergic congestion, congestion, hypotension, cardiovascular disease, diseases of the gastrointestinal tract, hyper- and hypo-motility and acidic secretion of the gastrointestinal tract, comprising administering the salt of the compound of formula 1 to a mammal in need of such treatment.

The invention also relates to a process for the preparation of the tosylate salt of the compound of formula 1 comprising the steps of
(i) contacting the compound of formula 1 dissolved in a suitable solvent with para-toluenesulfonic acid (commonly referred to as tosic acid); and
(ii) collecting the crystals formed.

The present invention also relates to the tosylate salt of trans-N-isobutyl-3-fluoro-3-[3-fluoro-4-(pyrrolidin-1-ylmethyl)phenyl]cyclobutanecarboxamide (1) prepared in accordance with the process of the invention.

BRIEF DESCRIPTION OF THE DRAWINGS

FIG. 1 provides a complete tabulation of relative intensities of observed peaks in the observed X-ray powder diffraction pattern of the tosylate salt of trans-N-isobutyl-3-fluoro-3-[3-fluoro-4-(pyrrolidin-1-ylmethyl)phenyl]cyclobutanecarboxamide.

FIG. 5 provides determined VTI moisture sorption data for a step isotherm using water as absorbate, for the tosylate salt of trans-N-isobutyl-3-fluoro-3-[3-fluoro-4-(pyrrolidin-1-ylmethyl)phenyl]cyclobutanecarboxamide.

DETAILED DESCRIPTION OF THE INVENTION

The compound of formula 1 is an antagonist of the histamine-3 ($H_3$) receptor, and is useful in the treatment of a number of CNS diseases, disorders and conditions. The free base of the compound and its hydrochloride salt may be prepared in accordance with the methods set forth in U.S. Ser. No. 11/549,175, filed Oct. 13, 2006 (see also "Histamine-3 Receptor Antagonists". WO2007/049123). The tosylate salt may be prepared under a variety of different conditions. In one embodiment of the process, the free base of the compound of formula 1 is preferably dissolved in a suitable solvent until completely dissolved, whereupon para-toluenesulfonic acid is added to the solution thereby prepared to create the tosylate addition salt of the invention. Suitable solvents include ethyl acetate, methyl acetate, isopropyl acetate, methanol, ethanol, n-propanol, isopropanol, tert-butanol, diethyl ether, di-isopropyl ether and methyl tert-butyl ether; preferably ethyl acetate or methanol. In another embodiment of the process, the contacting of the compound of formula 1 in solution phase is completed with either a solution of para-toluenesulfonic acid or the solid form of para-toluenesulfonic acid.

Preferably, the contacting step is carried out over a period of between 1 and 24 hours, more preferably between 10 and 20 hours, and comprising stirring or mixing the resulting mixture. A preferred embodiment of the process is wherein step (i) of the process is run between ambient temperature and the refluxing temperature of the solvent; more preferably, between ambient temperature and about 80° C.; most preferably, the process is run between 25° C. and 60° C. The preferred suitable solvent is ethyl acetate or methanol. Preferably, the reaction mixture is allowed to cool to ambient temperature once the addition of para-toluenesulfonic acid is complete and permitted to stir for the remainder of the reaction period. In a preferred embodiment, please see the protocol of Example 1.

Physical Characterization

I(a). Crystallinity

A sample was prepared in silicon oil and observed under cross-polarized light. This lot is crystalline and contains highly birefringent needle shaped particles. No amorphous particles were observed in this sample.

I(b). Powder X-Ray Diffraction

The tosylate salt of the invention was determined to be crystalline using powder x-ray diffraction. A powder x-ray diffraction pattern was collected for the tosylate salt of the invention, using a Bruker D5000 diffractometer (Madison, Wis.) equipped with a copper radiation source, fixed slits (divergence 1.0 mm, antiscatter 1.0 mm, and receiving 0.6 mm) and a Solex solid-state detector. Data was collected in the theta-two (2θ) theta goniometer configuration from a flat plate sample holder at the Copper wavelength $K\alpha_1=1.54056$ and $K\alpha_2=1.54439$ (relative intensity 0.5) from 3.0 to 40.0 degrees two-theta using a step size of 0.040 degrees and a step time of one second. X-ray tube voltage and amperage were set at 40 kV and 30 mA respectively.

Data were collected and analyzed using Bruker DIFFRAC Plus software. Samples were prepared by placing them in a quartz holder. (It is noted that a Bruker D5000 diffractometer is similar in operation to Siemans model D5000.) The results are summarized in Table 1 which provides the two-theta values and relative intensities for all of the reflections (lines) that have a relative intensity greater than or equal to 7% using a reflection width of 0.30 and a threshold of 4.0.

TABLE I

Powder X-ray Diffraction Reflections for Tosylate Salt

| Angle $2\theta \pm 0.2°$ | Relative Intensity* % |
|---|---|
| 8.35 | 100 |
| 9.305 | 10.6 |
| 9.512 | 7.2 |
| 11.128 | 9.2 |
| 12.103 | 9.2 |
| 13.401 | 17.7 |
| 16.681 | 57.6 |
| 18.094 | 11.1 |
| 18.513 | 11.4 |
| 19.096 | 36.8 |
| 19.582 | 12.9 |
| 20.579 | 18.9 |
| 21.54 | 32.9 |
| 22.21 | 39.2 |
| 24.872 | 13.9 |
| 25.492 | 7.6 |
| 26.028 | 13.1 |
| 27.156 | 7.8 |

*The relative intensity may vary depending on particle size and shape.

The present invention includes the tosylate salt of the compound of formula 1 wherein the principal X-ray diffraction pattern peaks expressed in terms of 2θ as measured with copper ($K\alpha_1=1.54056$, $K\alpha_2=1.54439$) radiation includes any combination of the peaks in Table I, and as fully compiled in FIG. 1. FIG. 2A shows quantification of the major peak, heights that were determined. For example, the present invention includes the tosylate salt of the compound of formula 1 wherein the principal X-ray diffraction pattern peaks expressed in terms of 2θ (±0.2) are 100, 10.6, 7.2, 9.2, 9.2, 17.7, 57.6, 11.1, 11.4 etc., or any subset thereof or individual peak thereof, e.g., 100, 10.6, 7.2, and all others, together or individually. FIG. 2B shows quantification of all peak heights detected.

2. Thermal Analysis

Figure 3:
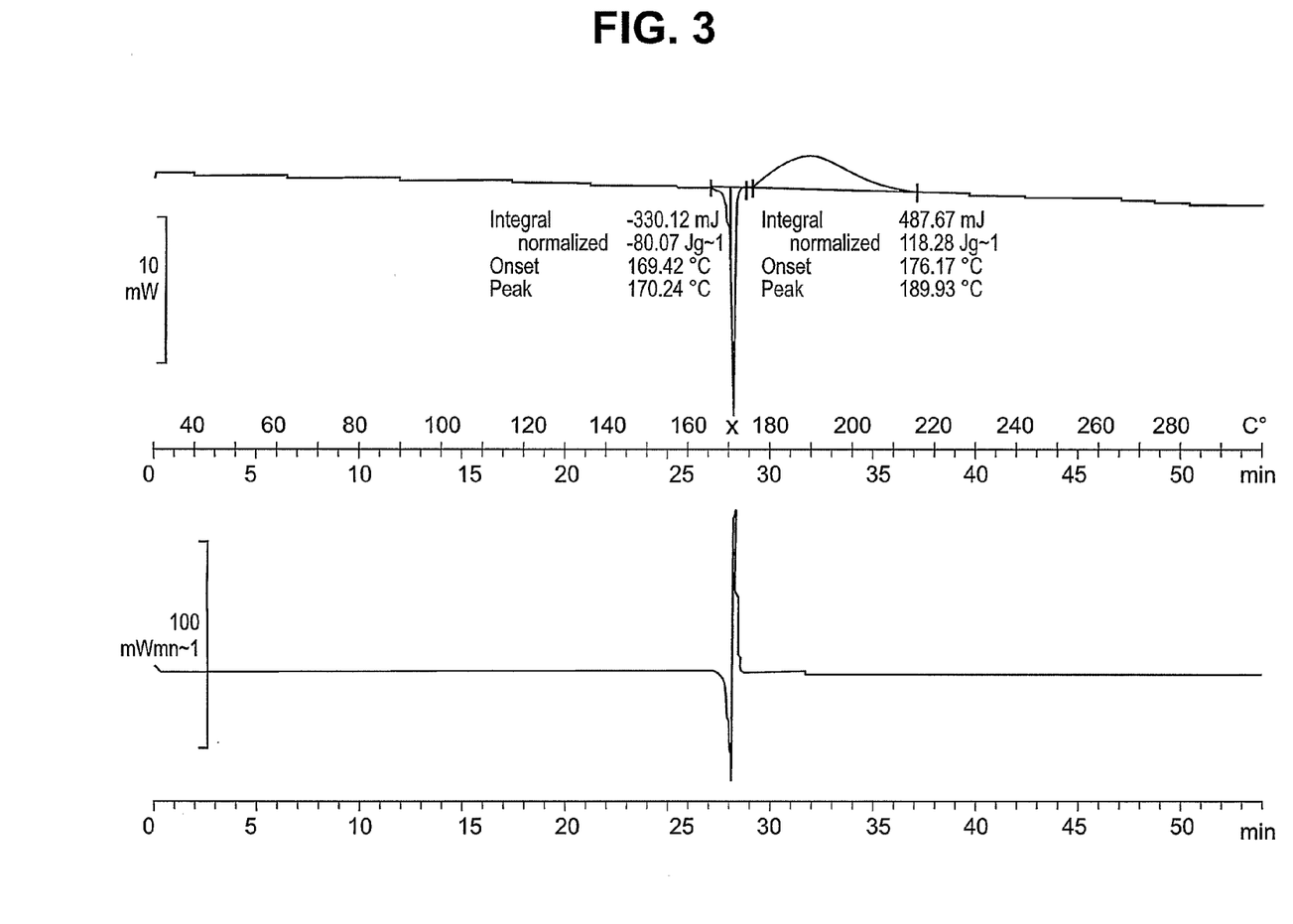
FIG. 3 provides a differential scanning calorimetry trace of a 4.1230 mg sample of the tosylate salt of trans-N-isobutyl-3-fluoro-3-[3-fluoro-4-(pyrrolidin-1-ylmethyl) phenyl]cyclobutane carboxamide, run from 30° C. to 300° C. at 5.00° C./min, with the two predominant events being described as (A) integral −330.12 mJ, normalized −80.07 Jg $^{-1}$, onset 169.42° C., peak 170.24° C.; and (B) integral 487.67 mJ, normalized 118.28 Jg $^{-1}$, onset 176.17° C., peak 189.93° C.
Figure 4:
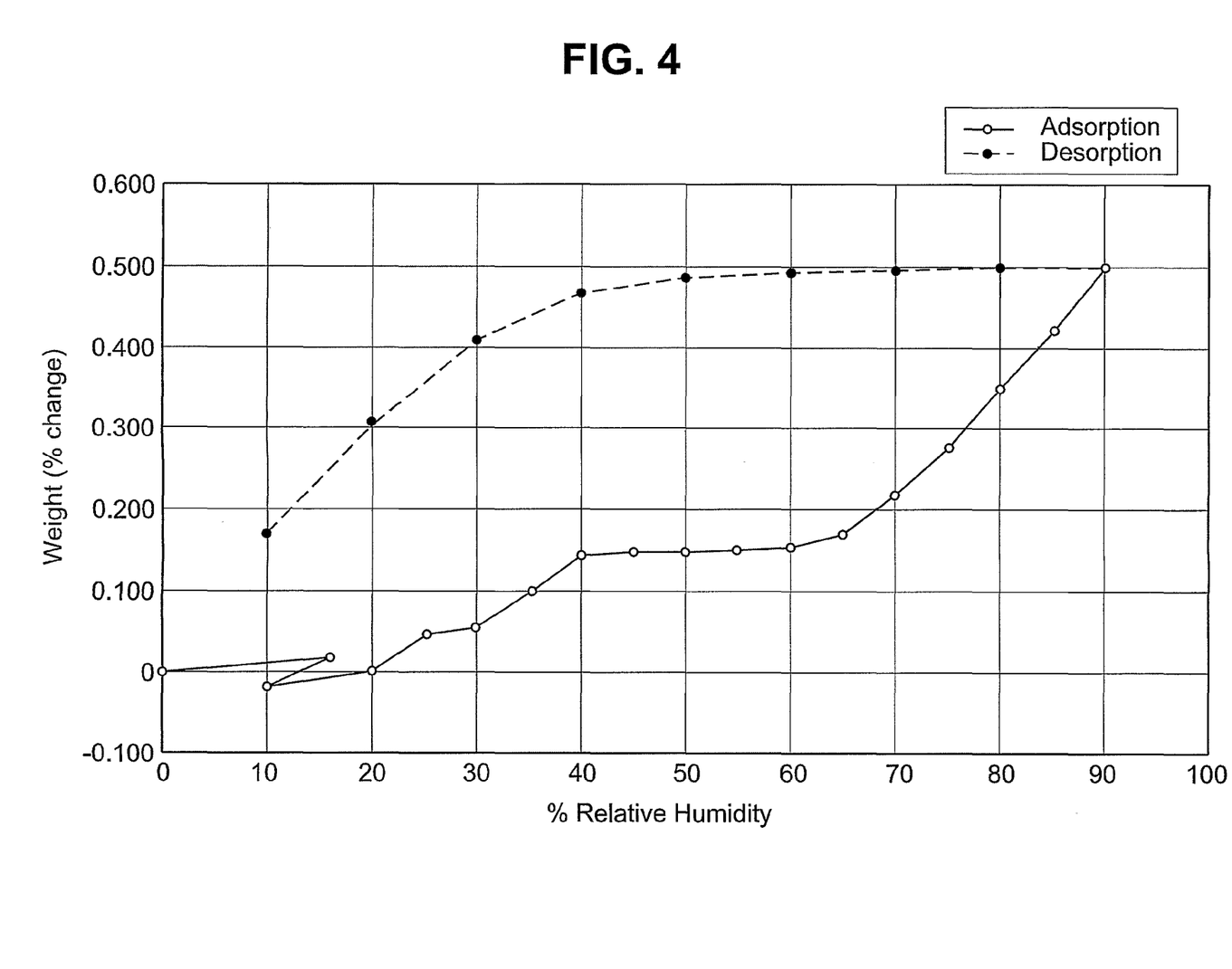
FIG. 4 provides a moisture sorption isotherm of the tosylate salt of trans-N-isobutyl-3-fluoro-3-[3-fluoro-4-(pyrrolidin-1-ylmethyl)phenyl]cyclobutanecarboxamide, with adsorption as lower curve and desorption as upper curve, plotting percent change in weight as a function of relative humidity, using the kinetic flow through method (17.17 mg, 25° C.).

Differential scanning calorimetry was performed in an aluminum pan with a pin hole in the lid from 30° C. to 300° C. at a heating rate of 5° C./minute. A single endothermic event was detected $T_{onset}$ approximately 169° C. An exothermic event occurs immediately after the melting. The profile is shown in FIG. 3. A plot of the adsorption/desorption isotherms (as conducted via the kinetic flow through method) is shown in FIG. 4.

Hot stage microscopy confirmed that the endothermic transition observed in the DSC trace corresponds to the melting event. A sample was prepared in silicon oil and observed under cross polarized light as it was heated from room temperature to 160° C. at 10° C./min and then from 160° C. to 200° C. at 5° C./min. The particles started to melt at T (approx) 164° C. with the melt being complete by T 167° C. Browning of the melt was not observed and crystallization of the cooled melt did not occur.

3. Hygroscopicity

During the initial drying cycle (25° C., 1-3% RH), approximately 0.8% weight loss was observed, which is consistent with an anhydrous form. The sample gained 0.5% of its original weight when exposed to relative humidities from 0% to 90% at 25° C. (CQG≦2% wt. gain at 90% RH). The hygroscopicity data generated in this kinetic experiment (VTI) suggests that the product is very slightly hygroscopic. FIG. 5 (VTI Moisture Sorption Data) reports results achieved in a step isotherm at a heating rate of 1° C./minute.

4. Solubility

The following information was determined in regard of aqueous solubility. The tosylate salt of the invention has a solubility of 5.0 mgA/mL in 0.1M phosphate buffered saline (final pH 6.3); a solubility of 7.0 mgA/mL in 0.1M phosphate buffered saline with 0.5 weight percent of sodium taurocholate/phosphatidyl choline salts at a final pH of 7.4; and 8.4 mgA/m L in unbuffered water (final pH 4.7). These values represent the solubility of the crystalline compound determined via RP-HPLC analysis after subjecting the drug media mixture to a temperature cycling program (40° C. for 8 hours, 15° C. for 5 hours, and 25° C. for 12 hours). The apparent solubility of the tosylate salt of the invention in simulated gastric fluid, with no enzymes, was between 7.1 and 14.2 mgA/mL.

The tosylate salt of the present invention may be provided, for example, as solid plugs, powders, or films by methods such as precipitation, crystallization, freeze drying, spray drying, or evaporative drying. Microwave or radio frequency drying may be used for this purpose.

The tosylate salt may be administered alone or in combination with one or more other drugs. Generally, these compositions will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

The tosylate salt of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The tosylate salt of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula I, a film-forming polymer, a binder, a solvent, a humectant, a plasticizer, a stabilizer or emulsifier, a viscosity-modifying agent and a solvent. Some components of the formulation may perform more than one function.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavorings and flavor enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line*, 25(2), 1-14, by Verma et al (2001). The use of chewing gum to achieve controlled release is described in WO 00/35298.

The tosylate salt of the invention may also be administered directly into the blood stream, into muscle, or into an internal organ. Suitable means for parenteral administration include intravenous, intra-arterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of the tosylate salt of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

The tosylate salt of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J. Pharm. Sci., 88 (10), 955-958, by Finnin and Morgan (October 1999).

Other means of topical administration include delivery by electroporation, iontophoresis, phonophoresis, sonophoresis and microneedle or needle-free (e.g. Powderject™ Bioject™, etc.) injection.

Formulations for topical administration may be formulated to be immediate and/or modified release. Modified release formulations include delayed-, sustained-, pulsed-, controlled-, targeted and programmed release.

The tosylate salt of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurized container, pump, spray, atomizer (preferably an atomizer using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurized container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine; mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µl to 100 µl. A typical formulation may comprise a compound of formula I, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted- and programmed-release.

In the case of dry powder inhalers and aerosols, the dosage unit is determined by means of a valve which delivers a metered amount. Units in accordance with the invention are typically arranged to administer a metered dose or "puff" containing from 1 µg to 20 mg of the compound of formula I. The overall daily dose will typically be in the range 1 mg to 200 mg which may be administered in a single dose or, more usually, as divided doses throughout the day.

The tosylate salt of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The tosylate salt of the invention may also be administered directly to the eye or ear, typically in the form of drops of a micronised suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The tosylate salt of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains the tosylate salt of the compound of formula I in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

The tosylate salt of the invention can be administered via either the oral, transdermal (e.g., through the use of a patch), intranasal, sublingual, rectal, parenteral or topical routes. Transdermal and oral administration are preferred. The active salt is, most desirably, administered in dosage ranging from about 0.001 mg/kg up to about 50 mg/kg per day, preferably from about 0.01 mg/kg to about 50 mg/kg per day in single or divided doses, although variations will necessarily occur depending on the weight and condition of the subject being treated and the particular route of administration chosen. However, a dosage level that is in the range of about 0.01 mg/kg to about 10 mg/kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing harmful side effects, provided that such larger doses are first divided into several small doses for administration throughout the day. The dosage amounts set forth in this description and in the appended claims may be used, for example, for an average human subject having a weight of about 60 kg to about 70 kg. The skilled practitioner will readily be able to determine any variation in the dosage amount that may be required for a subject whose weight falls outside the about 60 kg to about 70 kg range, such as infants and the elderly, based upon the medical history of the subject. The pharmaceutical combinations may be administered on a regimen of up to 6 times per day, preferably 1 to 3 times per day, such as 2 times per day or once daily.

For the avoidance of doubt, references herein to "treatment" include references to curative, palliative and prophylactic treatment.

The following example illustrates the method and compound of the present invention. It will be understood, however, that the invention is not limited to this specific Example.

Example 1

Tosylate Salt of trans-N-isobutyl-3-fluoro-3-[3-fluoro-4-pyrrolidin-1-ylmethyl)phenyl]-cyclo-butan-ecarboxamide (1)

3-Fluoro-3-(3-fluoro-4-pyrrolidin-1-ylmethyl-phenyl)-cyclobutanecarboxylic acid isobutyl-amide. (13.8 g, 79.0 mmol) was dissolved in EtOAc (250 mL) and p-toluenesulfonic acid (15.2 g, 79.9 mmol) in EtOAc (150 mL) was added. The resulting solution was stirred overnight and the white precipitate was collected and dried under nitrogen purge to yield 16.5 g of mono-tosylate salt. The salt was dissolved first with heating in a mixture of 20 mL MeOH and 40 mL EtOAc. Following filtration through a nylon filter, EtOAc (250 mL) was added over ~40 min. After stirring an additional hour, the resulting white solid was collected and dried under nitrogen purge. This recrystallization procedure was repeated two more times to afford 12.19 g of material that was 99.44% pure as determined by HPLC analysis: LRMS m/z Calcd for $C_{20}H_{28}F_2N_2O$, 350.2. found, 351.2 (M+H) APCI. $^1$H-NMR (CDCl$_3$) δ 7.79-7.24 (m, 3H), 7.32-7.28 (m, 2H), 7.19 (d, J=7.9 Hz, 2H), 5.78 (br s, 1H), 4.32 (d, J=5.4 Hz, 2H), 3.79-3.73 (m, 2H), 3.29 (p, J=6.4 Hz, 1H), 3.10-3.07 (m, 2H), 2.93-2.66 (m, 6H), 2.36 (s, 3H), 2.24-2.18 (m, 2H), 2.08-2.02 (m, 2H), 1.76 (hept, 6.7 Hz, 1H), 0.89 (d, J=6.6 Hz, 6H); $^{13}$C-NMR (CDCl$_3$) δ 174.0, 161.3 (d, $J_{C-F}$=248.7 Hz), 147.4 (dd, $J_{C-F}$=24.0, 7.5 Hz), 142.5, 140.3, 133.6 (d, $J_{C-F}$=2.3 Hz), 129.1, 126.1, 121.8 (dd, $J_{C-F}$=8.7, 3.3 Hz), 116.4 (d, $J_{C-F}$=14.3 Hz), 112.6 (dd, $J_{C-F}$=23.7, 9.4 Hz), 96.7 (d, $J_{C-F}$=196.9 Hz), 53.4, 50.3, 47.2, 38.9 (d, $J_{C-F}$=24.8 Hz), 32.8, 28.7, 23.0, 21.5, 20.3; Elemental analysis calculated for $C_{20}H_{28}F_2N_2O\cdot C_7H_8O_3S$, C, 62.05; H, 6.94; N, 5.36; F 7.27; S 6.14. Found C, 61.85; H, 7.03; N, 5.32; F, 7.21; S, 6.34, with a molecular weight of 522.66.

The invention claimed is:

1. A crystalline form of the tosylate salt of a compound of formula 1:

having an x-ray diffraction pattern characterized substantially by x-ray diffraction pattern peaks as measured with copper (Kα$_1$=1.54056, Kα$_2$=1.54439) radiation at 2θ (±0.2) of 8.35, 13.401, 16.681, 19.096, 19.582, 20.579, 21.54 and 22.21.

2. The compound according to claim 1 having an x-ray diffraction pattern characterized substantially by x-ray diffraction pattern peaks as measured with copper (Kα$_1$=1.54056, Kα$_2$=1.54439) radiation at 2θ (±0.2) of 8.35, 9.305, 9.512, 11.128, 12.103, 13.401, 16.681, 18.094, 18.513, 19.096, 19.582, 20.579, 21.54, 22.21, 24.872, 25.492, 26.028 and 27.156 .

* * * * *